(12) United States Patent
Akagane

(10) Patent No.: US 10,046,362 B2
(45) Date of Patent: Aug. 14, 2018

(54) VIBRATION GENERATING UNIT, VIBRATING BODY UNIT, AND ULTRASONIC TREATMENT APPARATUS

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/074,192

(22) Filed: Mar. 18, 2016

(65) Prior Publication Data

US 2016/0199881 A1 Jul. 14, 2016

Related U.S. Application Data

(63) Continuation of application No. PCT/JP2014/078625, filed on Oct. 28, 2014.

(30) Foreign Application Priority Data

Nov. 15, 2013 (JP) .................................. 2013-237252

(51) Int. Cl.
*A61B 17/32* (2006.01)
*B06B 3/02* (2006.01)
(Continued)

(52) U.S. Cl.
CPC ........ *B06B 3/02* (2013.01); *A61B 17/320068* (2013.01); *A61B 17/320092* (2013.01);
(Continued)

(58) Field of Classification Search
CPC .... A61B 17/320068; A61B 17/320092; A61B 2017/0011; A61B 17/22004;
(Continued)

(56) References Cited

U.S. PATENT DOCUMENTS 5,516,043 A * 5/1996 Manna .................. B05B 17/063
239/102.2
6,058,823 A 5/2000 Michoud
(Continued)

FOREIGN PATENT DOCUMENTS

CN 101674782 A 3/2010
JP H02-40473 U 3/1990
(Continued)

OTHER PUBLICATIONS

Jan. 20, 2015 International Search Report issued in International Patent Application No. PCT/JP2014/078625.
(Continued)

*Primary Examiner* — Ryan J Severson
*Assistant Examiner* — Christian Knauss
(74) *Attorney, Agent, or Firm* — Oliff PLC

(57) ABSTRACT

A vibration generating unit includes a proximal side vibration transmitting section extended from a proximal end of the ultrasonic transducer toward a proximal direction. A proximal end of the proximal side vibration transmitting section is placed at a position apart from a reference antinode position toward the proximal direction by an extending dimension equal to an integral multiple of a half wavelength, when the reference antinode position is the closest to the ultrasonic transducer among antinode positions placed on the proximal direction side with respect to the ultrasonic transducer. The vibration generating unit includes an amplitude increasing section increasing an amplitude of the ultrasonic vibration transmitted toward the proximal direction in the proximal side vibration transmitting section.

8 Claims, 12 Drawing Sheets

(51) Int. Cl.
   *B06B 1/06* (2006.01)
   *B06B 3/00* (2006.01)
   *A61N 1/04* (2006.01)
   *A61N 1/36* (2006.01)
   *A61B 17/00* (2006.01)
   *A61B 17/22* (2006.01)

(52) U.S. Cl.
   CPC ......... *A61N 1/0476* (2013.01); *A61N 1/0484* (2013.01); *A61N 1/36025* (2013.01); *B06B 1/06* (2013.01); *B06B 3/00* (2013.01); *A61B 2017/0003* (2013.01); *A61B 2017/00106* (2013.01); *A61B 2017/22018* (2013.01)

(58) Field of Classification Search
   CPC .......... A61B 2017/00106; A61B 2017/22018; B06B 3/00; B06B 3/02; B06B 1/06; A61N 7/00
   See application file for complete search history.

(56) References Cited

U.S. PATENT DOCUMENTS 6,077,285 A * 6/2000 Boukhny ............ B06B 1/0611
                                                     604/22
   2002/0029054 A1 * 3/2002 Rabiner ........... A61B 17/3206
                                                     606/169
   2002/0036444 A1   3/2002 Yamashiro et al.
   2005/0070800 A1 * 3/2005 Takahashi ........ A61B 17/32009
                                                     600/459
   2008/0234711 A1   9/2008 Houser et al.
   2012/0293044 A1  11/2012 Bromfield
   2013/0274637 A1  10/2013 Akagane

FOREIGN PATENT DOCUMENTS

JP    H07-16254    A    1/1995
   JP    H11-514935   A   12/1999
   JP    2001-205189  A    7/2001
   JP    2002-035001  A    2/2002
   JP    2002-254044  A    9/2002
   JP    2008-238390  A   10/2008
   WO    2009/070462  A1   6/2009
   WO    2013/027614  A1   2/2013

OTHER PUBLICATIONS

Aug. 4, 2015 Office Action issued in Japanese Patent Application No. 2015-527379.
May 26, 2016 International Preliminary Report on Patentability issued in International Patent Application No. PCT/JP2014/078625.
Jun. 2, 2017 European Search Report issued in European Patent Application No. 14861721.0.
Sep. 1, 2017 Office Action issued in Chinese Patent Application No. 201480062189.5.

* cited by examiner

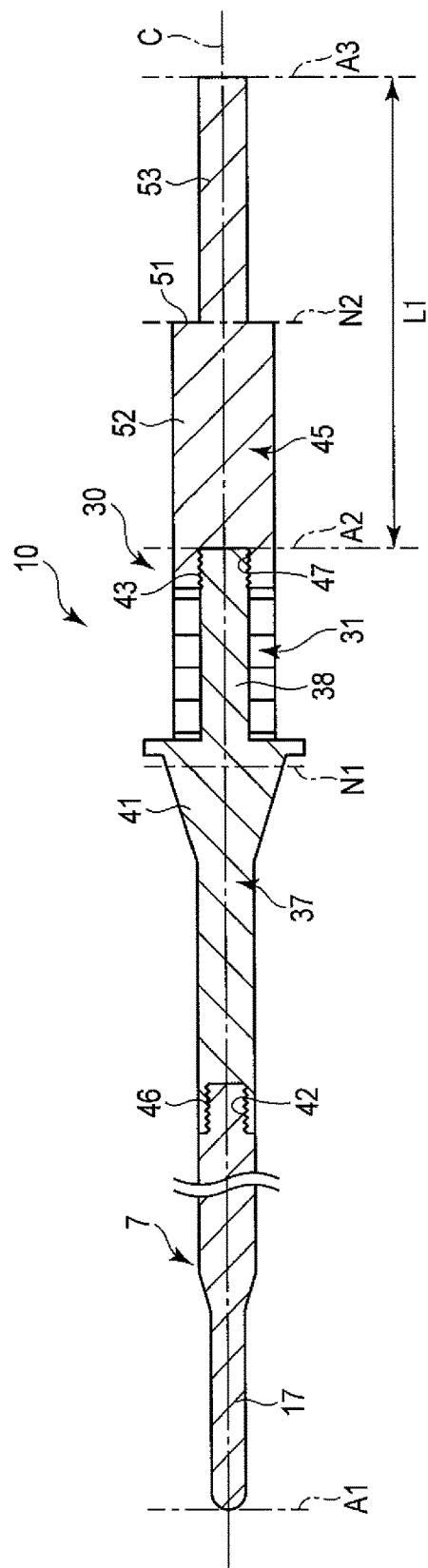
F I G. 4

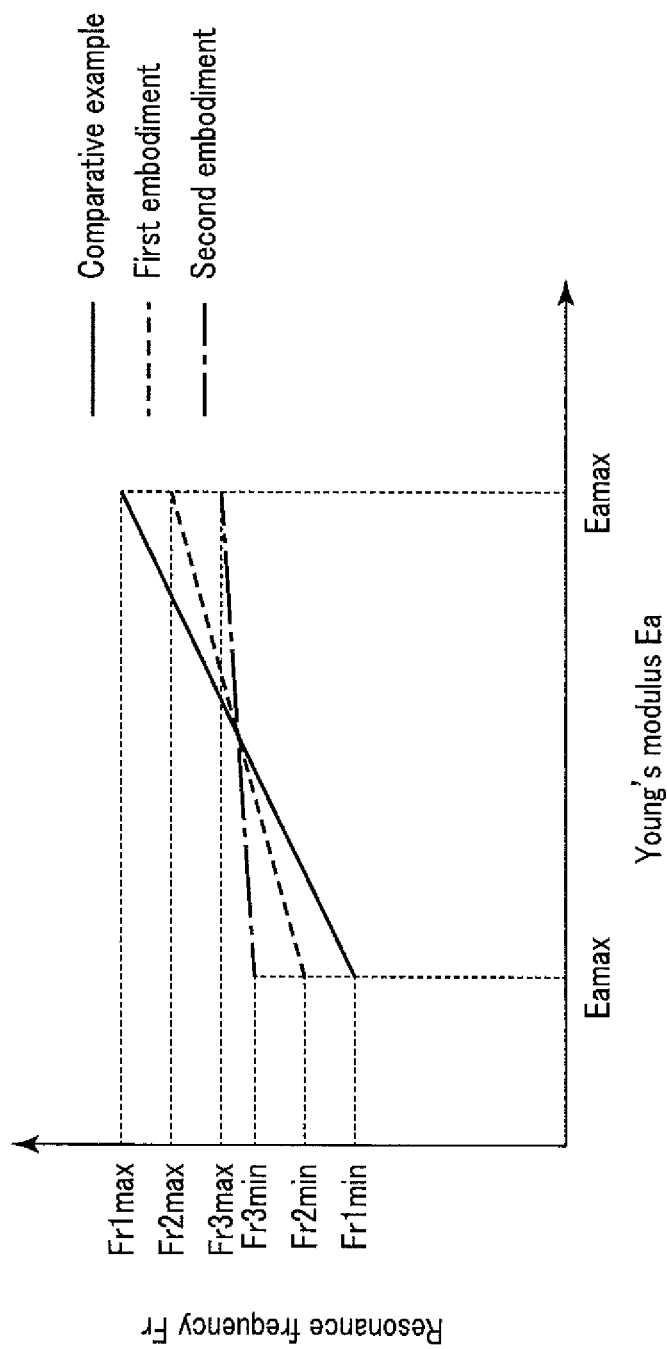
F I G. 8

VIBRATION GENERATING UNIT, VIBRATING BODY UNIT, AND ULTRASONIC TREATMENT APPARATUS

CROSS-REFERENCE TO RELATED APPLICATIONS

This is a Continuation Application of PCT Application No. PCT/JP2014/078625, filed Oct. 28, 2014 and based upon and claiming the benefit of priority from prior Japanese Patent Application No. 2013-237252, filed Nov. 15, 2013, the entire contents of which are incorporated herein by reference.

BACKGROUND OF THE INVENTION

1. Field of the Invention

The present invention relates to a vibration generating unit configured to generate an ultrasonic vibration for use in a treatment in an ultrasonic treatment apparatus in which a treatment section gives a treatment to a treated target by using the ultrasonic vibration. Further, the present invention also relates to a vibrating body unit including the treatment section and the vibration generating unit, and to the ultrasonic treatment apparatus including the vibrating body unit.

2. Description of the Related Art

Jpn. Pat. Appln. KOKAI Publication No. Hei 7-16254 discloses an ultrasonic treatment apparatus including a surgery tip provided in a distal portion thereof as a treatment section. In this ultrasonic treatment apparatus, a vibration generating unit including a piezoelectric crystal (a piezoelectric element) configured to convert an electric current into an ultrasonic vibration is provided. On a distal direction side of the vibration generating unit, a vibration transmitting rod is extended. On a distal direction side of the vibration transmitting rod, the surgery tip is attached. The ultrasonic vibration generated by the piezoelectric crystal is transmitted from the proximal direction toward the distal direction through the vibration transmitting rod. Further, the surgery tip gives a treatment to a treated target such as a biological tissue by using the transmitted ultrasonic vibration. The vibration transmitting rod and the surgery tip form a distal side vibration transmitting section which is connected to the distal direction side of the vibration generating unit, and to which the ultrasonic vibration is transmitted from the vibration generating unit. Furthermore, the vibration generating unit, the vibration transmitting rod, and the surgery tip form a vibrating body unit.

BRIEF SUMMARY OF THE INVENTION

According to one aspect of the invention, a vibration generating unit with which a distal side vibration transmitting section is connected from a distal direction side, the distal side vibration transmitting section including a treatment section configured to treat a biological tissue and provided in a distal portion thereof, and the vibration generating unit being configured to generate an ultrasonic vibration transmitted to the distal side vibration transmitting section, the vibration generating unit including: a connecting section with which the distal side vibration transmitting section is connected; an ultrasonic transducer including a piezoelectric element which is configured to generate the ultrasonic vibration; a transducer attachment section to which the ultrasonic transducer is attached; a proximal side vibration transmitting section which is extended from a proximal end of the ultrasonic transducer toward a proximal direction along a longitudinal axis, a proximal end of the proximal side vibration transmitting section being placed at a position apart from a reference antinode position toward the proximal direction by an extending dimension equal to an integral multiple of a half wavelength of the ultrasonic vibration, when the reference antinode position is an antinode position closest to the ultrasonic transducer among antinode positions of the ultrasonic vibration placed on the proximal direction side with respect to the ultrasonic transducer; and an amplitude increasing section which is provided between the proximal end of the proximal side vibration transmitting section and the reference antinode position in an axis parallel direction parallel to the longitudinal axis, and which is configured to increase an amplitude of the ultrasonic vibration transmitted toward the proximal direction in the proximal side vibration transmitting section, the amplitude increasing section being placed at a node position closest to the reference antinode position among node positions of the ultrasonic vibration placed on the proximal direction side with respect to the reference antinode position.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a cross-sectional view schematically showing the vibrating body unit according to the first embodiment;

FIG. 8 is a schematic view showing a relationship between the Young's modulus of an ultrasonic probe and a resonance frequency of the vibrating body unit in each of the comparative example, the first embodiment, and the second embodiment;

DETAILED DESCRIPTION OF THE INVENTION

Verification of Vibration State as Reference of Embodiments

Figure 1:
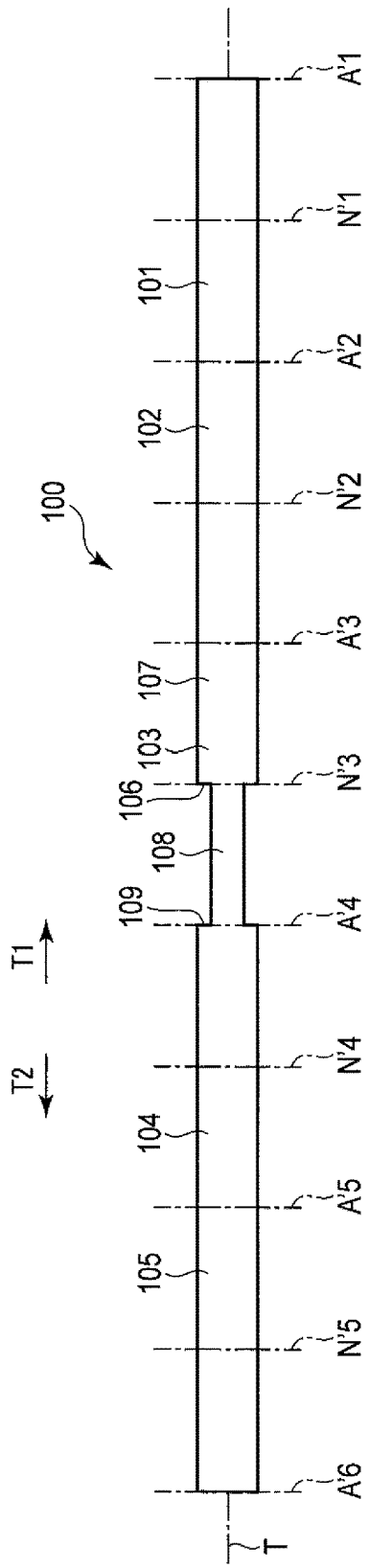
FIG. 1 is a schematic view showing a test vibrating body used in verification of a vibration state which can be a reference of embodiments according to the present invention.

Before describing embodiments according to the present invention, verification of a vibration state which can be a reference of later-described embodiments will now be described with reference to FIG. 1. FIG. 1 is a view showing a test vibrating body 100 used in verification of a vibration state. The verification of a vibration state is carried out by, e.g., simulation, and a relationship between the Young's modulus (E) and a resonance frequency (Fr) is verified with the use of a test vibrating body 100.

As shown in FIG. 1, the test vibrating body 100 is extended along an extension axis T. Here, one side of directions parallel to the extension axis T is determined as a first extending direction (a direction of an arrow T1 in FIG. 1), and an opposite direction of the first extending direction is determined as a second extending direction (a direction of an arrow T2 in FIG. 1). In the test vibrating body 100, an ultrasonic vibration is transmitted from the first extending direction toward the second extending direction. Moreover, the test vibrating bod 100 has antinode positions A'1 to A'6 and node positions N'1 to N'5. That is, the test vibrating body 100 vibrates in a predetermined vibration state having the antinode positions A'1 to A'6 and the node positions N'1 to N'5 by transmitting the ultrasonic vibration.

In the test vibrating body 100, a first transmitting region 101, a second transmitting region 102, a third transmitting region 103, a fourth transmitting region 104, and a fifth transmitting region 105 are sequentially extended from the first extending direction. The first transmitting region 101 is extended between the antinode position A'1 and the antinode position A'2, the second transmitting region 102 is extended between the antinode position A'2 and the antinode position A'3, the third extending region 103 is extended between the antinode position A'3 and the antinode position A'4, the fourth transmitting region 104 is extended between the antinode position A'4 and the antinode position A'5, and the fifth transmitting region 105 is extended between the antinode position A'5 and the antinode position A'6.

The third transmitting region 103 includes a cross-sectional area reducing section 106, a first extending section 107 extended from the cross-sectional area reducing section 106 toward the first extending direction, and a second extending section 108 extended from the cross-sectional area reducing portion 106 toward the second extending direction. When the test vibrating body 100 vibrates in a predetermined vibration state, the node position N'3 on which stress caused by the ultrasonic vibration acts is placed at the cross-sectional area reducing section 106. Additionally, a cross-sectional area of the second extending section 108 perpendicular to the extension axis T is smaller than that of the first extending section 107 due to the cross-sectional area reducing section 106. Since the cross-sectional area perpendicular to the extension axis T is reduced at the position where the stress caused by the ultrasonic vibration acts is reduced, an amplitude of the ultrasonic vibration is increased (raised) at the cross-sectional area reducing section 106. It is to be noted that each of the first transmitting region 101, the second transmitting region 102, and the first extending section 107 of the third transmitting region 103 has a cross-sectional S1 perpendicular to the extension axis T. Further, in the second extending section 108 of the third transmitting region 103, a cross-sectional area perpendicular to the extension axis T is S2, which is smaller than the cross-sectional area S1.

Furthermore, a cross-sectional area increasing section 109 is provided at the antinode position A'4 between the third transmitting region 103 and the fourth transmitting region 104. That is, when the test vibrating body 100 vibrates in a predetermined vibration state, the antinode position A'3 is placed at the cross-sectional area increasing section 109. A cross-sectional area of the fourth transmitting region 104 perpendicular to the extension axis T becomes larger than that of the second extending section 108 of the third transmitting region 103 by the cross-sectional area increasing section 109. However, at the antinode position A'3 placed at the cross-sectional area increasing section 109, the stress caused by the ultrasonic vibration becomes zero. Since the stress caused by the ultrasonic vibration does not act, in the cross-sectional area increasing section 109, the amplitude of the ultrasonic vibration is not reduced (not changed) even if the cross-sectional area perpendicular to the extension axis T is increased (changed). It is to be noted that a cross-sectional area perpendicular to the extension axis T in the fourth transmitting region 104 and the fifth transmitting region 105 is the same as that in the first transmitting region 101 and the second transmitting region 102, and it is hence S1.

In the verification of the vibration state, a relationship between the Young's modulus (E) and a resonance frequency (Fr) was verified by changing a transformation ratio (an increasing ratio) of the ultrasonic vibration in the cross-sectional area reducing section 106. That is, the verification was performed by changing a ratio of the cross-sectional area S1 of the first extending section 107 perpendicular to the extension axis T relative to the cross-sectional area S2 of the second extending section 108 perpendicular to the extension axis T. Further, at each transformation ratio, a change in the resonance frequency (Fr) of the test vibrating body 100 relative to a change in the Young's modulus (E) in the fourth transmitting region 104 was verified.

As a result of the verification, it was verified that the change in the Young's modulus (E) in the fourth transmitting region 104 further seriously affects the resonance frequency (Fr) of the test vibrating body 100 as the transformation ratio of the ultrasonic vibration in the cross-sectional area reducing section 106 increases. That is, as the amplitude of the ultrasonic vibration in the fourth transmitting region 104 increases, an influence of the Young's modulus (E) of the fourth transmitting region 104 on the resonance frequency (Fr) of the test vibrating body 100 becomes considerable. When the Young's modulus (E) of the fifth transmitting region 105 was changed, the same result in the case where the Young's modulus (E) of the fourth transmitting region 104 was changed was provided. That is, as the amplitude of the ultrasonic vibration in the fifth transmitting region 105 increases (as the transformation ratio of the ultrasonic vibration in the cross-sectional area reducing section 106 increases), an influence of the Young's modulus (E) of the fifth transmitting region 105 on the resonance frequency (Fr)

of the test vibrating body 100 becomes considerable. Thus, it was verified that the influence of the Young's modulus (E) on the resonance frequency (Fr) becomes larger in a region where the amplitude of the ultrasonic vibration increases.

Moreover, in the verification of the vibration state, at each transformation ratio, a change in the resonance frequency (Fr) of the test vibrating body 100 relative to a change in the Young's modulus (E) in the third transmitting region 103 was also verified. Since the second extending section 108 whose cross-sectional area S2 perpendicular to the extension axis T is reduced is provided in the third transmitting region 103, a volume of the third transmitting region 103 is smaller than that of each of the fourth transmitting region 104 and the fifth transmitting region 105. Thus, when the Young's modulus (E) in the third transmitting region 103 is changed, the relationship between the Young's modulus (E) and the resonance frequency (Fr) shows a tendency different from that in the case where the Young's modulus (E) is changed in the fourth transmitting region 104 (the fifth transmitting region 105).

In the above-described verification, the study was conducted about a reason why the tendency shown by the relationship between the Young's modulus (E) and the resonance frequency (Fr) differs depending on the case where the Young's modulus (E) is changed in the third transmitting region 103 and the case where the Young's modulus (E) is changed in the fourth transmitting region 104. Consequently, it was verified that a volume of a region whose Young's modulus is changed as well as the amplitude of the region whose Young's modulus is changed affects the relationship between the Young's modulus (E) and the resonance frequency (Fr). Actually, a volume of the third transmitting region 103 (i.e., the cross-sectional area S2 perpendicular to the extension axis T in the second extending section 108) affects the relationship between the Young's modulus (E) and the resonance frequency (Fr). That is, it was verified that an influence of the Young's modulus on the resonance frequency (Fr) increases in a region having a higher volume.

Embodiments according to the present invention will now be described hereinafter with reference to the result of the verification.

First Embodiment

Figure 2:
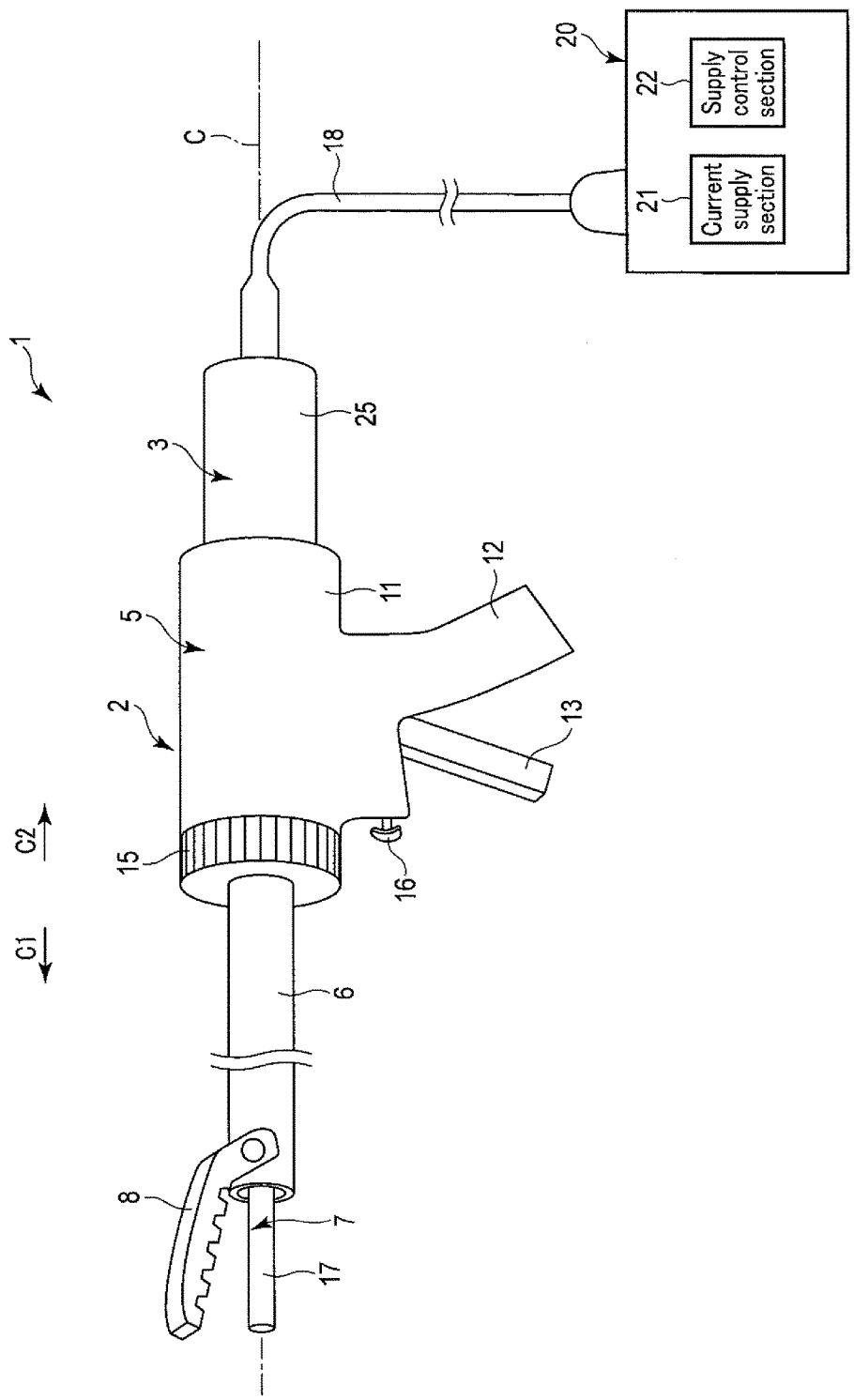
FIG. 2 is a schematic view showing an ultrasonic treatment apparatus according to a first embodiment of the present invention.

A first embodiment according to the present invention will now be described with reference to FIG. 2 to FIG. 5. FIG. 2 is a view showing a configuration of an ultrasonic treatment apparatus 1 according to this embodiment. As shown in FIG. 2, the ultrasonic treatment apparatus 1 includes a hand piece (a treatment unit) 2 which is an ultrasonic treatment instrument, and a transducer unit 3 coupled with the hand piece 2. The ultrasonic treatment apparatus 1 has a longitudinal axis C running through the hand piece 2 and the transducer unit 3. Here, one of directions parallel to the longitudinal axis C is determined as a distal direction (a direction of an arrow C1 in FIG. 2), and an opposite direction of the distal direction is determined as a proximal direction (a direction of an arrow C2 in FIG. 2). Moreover, the distal direction and the proximal direction are axis parallel directions parallel to the longitudinal axis C. The vibrator unit 3 is coupled with the hand piece 2 from the proximal direction side. The hand piece 2 is an ultrasonic incising-and-coagulation treatment instrument which simultaneously coagulates and incises a treated target such as a biological tissue by using an ultrasonic vibration.

The hand piece 2 includes a holding unit 5, a sheath 6, an ultrasonic probe 7 which is a distal side vibration transmitting section, and a jaw 8. The holding unit 5 includes a tubular case section 11 extended along the longitudinal axis C, a fixed handle 12 integrally formed with the tubular case section 11, and a movable handle 13 attached to the tubular case portion 11 to allow its turning motion. When the movable handle 13 pivots around a position at which it is attached to the tubular case section 11, the movable handle 13 opens or closes relative to the fixed handle 12. Additionally, the holding unit 5 includes a rotary operation knob 15 attached on the distal direction side of the tubular case section 11. The rotary operation knob 15 can rotate around the longitudinal axis C relative to the tubular case section 11. Further, a supply operation input button 16 which is a supply operation input section is disposed to the fixed handle 12.

The sheath 6 is extended along the longitudinal axis C. When the sheath 6 is inserted into the rotary operation knob 15 and into the tubular case section 11 from the distal direction side, the sheath 6 is attached to the holding unit 5. The ultrasonic probe 7 which is the distal side vibration transmitting section is extended along the longitudinal axis C from the inside of the tubular case section 11 toward the distal direction. Furthermore, the ultrasonic probe 7 is inserted through the sheath 6. A treatment section 17 protruding from the distal end of the sheath 6 toward the distal direction is provided in the ultrasonic probe 7.

The jaw 8 is attached to the distal portion of the sheath 6 to allow its turning motion. The movable handle 13 is connected to a movable tubular portion (not shown) of the sheath 6 inside the tubular case section 11. The distal end of the movable tubular portion is connected to the jaw 8. When the movable handle 13 is opened or closed relative to the fixed handle 12, the movable tubular portion moves along the longitudinal axis C. Consequently, the jaw 8 turns around the position at which it is attached to the sheath 6, and opens or closes relative to the treatment section 17 of the ultrasonic probe 7. Moreover, the sheath 6, the ultrasonic probe 7, and the jaw 8 can rotate around the longitudinal axis C relative to the tubular case section 11 integrally with the rotary operation knob 15.

One end of a cable 18 is connected to the proximal end of the transducer unit 3. The other end of the cable 18 is connected to an electric power supply unit 20. The electric power supply unit 20 includes a current supply section 21 configured to output an electric current, and a supply control section 22 configured to control the current supply section 21. The current supply section 21 is formed of, e.g., an electric power supply and an amplification circuit (a drive circuit) or the like, and the supply control section 22 is formed of, e.g., a CPU (Central Processing Unit) or an ASIC (application specific integrated circuit), and a storage section such as a memory. Additionally, the electric power supply unit 20 is an electric power supply device including, e.g., components, circuits, and others that form the current supply section 21 and the supply control section 22.

Figure 3:
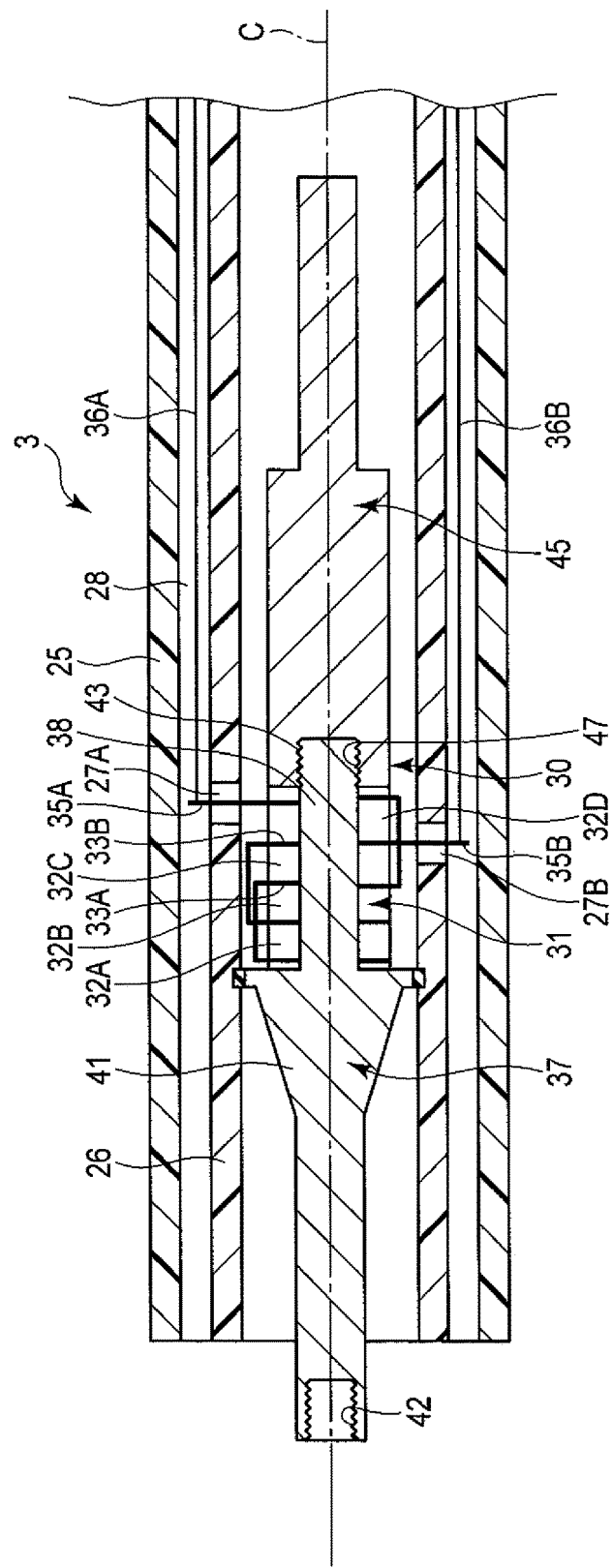
FIG. 3 is a cross-sectional view schematically showing a configuration of a transducer unit according to the first embodiment.

FIG. 3 is a view showing a configuration of the transducer unit 3. As shown in FIG. 3, the vibrator unit includes an outer transducer case 25, and an inner transducer case 26 placed inside the outer vibrator case 25. The outer transducer case 25 and the inner transducer case 26 are extended along the longitudinal axis C, and inserted into the tubular case section 11 of the holding unit 5 from the proximal direction side. Further, the outer vibrator case 25 and the inner vibrator case 26 are coupled with the sheath 6 inside the tubular case section 11.

A vibration generating unit 30 configured to generate an ultrasonic vibration is provided inside the inner transducer case 26. The outer transducer case 25, the inner transducer case 26, and the vibration generating unit 30 form the transducer unit 3. The vibration generating unit 30 includes an ultrasonic transducer 31. The ultrasonic transducer 31 includes (in this embodiment, four) piezoelectric elements 32A to 32D which convert an electric current into the ultrasonic vibration, and two electrode sections 33A and 33B.

Here, a direction to get away from the longitudinal axis C in a cross section perpendicular to the longitudinal axis C is determined as an outer peripheral direction (an adaxial direction), and the opposite direction of the outer peripheral direction is determined as an inner peripheral direction (an adaxial direction). Furthermore, the outer peripheral direction and the circumferential direction are determined as a radial direction. Two through holes 27A and 27B that are pierced in the inner transducer case 26 in the radial direction are formed in the inner transducer case 26. Moreover, a gap portion 28 is formed between the outer transducer case 25 and the inner transducer case 26 in the radial direction. The electrode section 33A includes a protruding portion 35A protruding from the through hole 27A to the gap portion 28 toward the outer peripheral direction. Additionally, the electrode section 33B includes a protruding portion 35B protruding from the through hole 27B to the gap portion 28 toward the outer peripheral direction.

One end of an electrical wiring 36A is connected to the protruding portion 35A of the electrode section 33A. Further, one end of an electrical wiring 36B is connected to the protruding portion 35B of the electrode section 33B. The electrical wirings 36A and 36B are extended through the gap portion 28 and an inside of the cable 18. The other end of each of the electrical wirings 36A and 36B is connected to the current supply section 21 of the electric power supply unit 20. When an electric current is supplied from the current supply section 21 to the ultrasonic vibrator 31 through the electrical wirings 36A and 36B, the ultrasonic transducer 31 generates the ultrasonic vibration.

The vibration generating unit 30 includes a columnar horn member 37 to which the ultrasonic oscillator 31 is attached. The horn member 37 is extended along the longitudinal axis C. The horn member 37 includes a transducer attachment section 38 to which the ultrasonic transducer 31 is attached. Furthermore, a cross-sectional area change section 41 is formed in the horn member 37 on the distal direction side with respect to the transducer attachment section 38. In the cross-sectional area change section 41, a cross-sectional area perpendicular to the longitudinal axis C is reduced from the proximal direction toward the distal direction. A female screw section 42 is formed in a distal portion of the horn member 38. The female screw section 42 is placed on the distal direction side with respect to the cross-sectional area change section 41. A male screw section 43 is formed in a proximal portion of the transducer attachment section 38. Moreover, the vibration generating unit 30 includes a columnar rod-shaped member 45 which is a proximal side vibration transmitting section extended along the longitudinal axis C in a part located on the proximal direction side with respect to the transducer attachment section 38.

The ultrasonic probe 7 is connected to the distal direction side of the vibration generating unit 30. The ultrasonic probe 7 is connected to the vibration generating unit 30 inside the tubular case section 11. When the ultrasonic probe 7 is connected to the vibration generating unit 30, a vibrating body unit 10 that vibrates by the ultrasonic vibration is formed.

FIG. 4 is a view showing a configuration of the vibrating body unit 10. As shown in FIG. 4, a male screw section 46 is formed in a proximal portion of the ultrasonic probe 7. When the male screw section 46 is screwed into the female screw section 42 of the horn member 37, the ultrasonic probe 7 is connected to the distal direction side of the horn member 37 of the vibration generating unit 30. A female screw section 47 is formed in a distal portion of the rod-shaped member 45. When the male screw section 43 of the vibrator attachment section 38 is screwed into the female screw section 47, the rod-shaped member 45 is connected to the proximal direction side of the horn member 37. The ultrasonic transducer 31 is attached to the transducer attachment section 38 in a state where it is sandwiched between the cross-sectional area change section 41 of the horn member 37 and the rod-shaped member 45. It is to be noted that the ultrasonic probe 7, the horn member 37, and the rod-shaped member 45 are made of materials having high transmissibility of the ultrasonic vibration such as Ti-6Al-4V.

When a supply operation is input by the supply operation input button 16 of the holding unit 5, an operation signal is transmitted to the supply control section 22 in the electric power supply unit 20 through an electrical signal path extended through the inner transducer case 26 and the inside of the cable 18. Consequently, the supply control section 22 controls the current supply section 21, and an electric current is supplied to the ultrasonic transducer 31 from the current supply section 21. Additionally, the ultrasonic vibration is generated by the ultrasonic vibrator 31.

The ultrasonic vibration generated by the ultrasonic transducer 31 is transmitted to the ultrasonic probe 7 through the horn member 37. At this time, an amplitude of the ultrasonic vibration is increased in the cross-sectional area change section 41 of the horn member 37. In the ultrasonic probe 7, the ultrasonic vibration is transmitted from the proximal direction toward the distal direction. Further, the treatment section 17 provided in the distal portion of the ultrasonic probe 7 gives a treatment to a treated target such as a biological tissue by using the transmitted ultrasonic vibration. Furthermore, the ultrasonic vibration generated by the ultrasonic transducer 31 is transmitted to the rod-shaped member 45. Moreover, in the rod-shaped member 45, the ultrasonic vibration is transmitted from the distal direction toward the proximal direction. It is to be noted that the vibrating body unit 10 performs a longitudinal vibration having a vibrating direction and a transmitting direction parallel to the longitudinal axis C depending on the ultrasonic vibration.

When the vibrating body unit 10 vibrates in a state where the treated target is grasped between the treatment section 17 of the ultrasonic probe 7 and the jaw 8, frictional heat is generated between the treatment section 17 and the treated target. The treated target is coagulated and incised at the same time by the generated frictional heat.

The vibrating body unit 10 vibrates at a resonance frequency Fr having antinode positions (e.g., A1 to A3) and node positions (e.g., N1 and N2). At this time, the distal end of the vibrating body unit 10 (the distal end of the ultrasonic probe 7) serves as the antinode position A1 of the ultrasonic vibration. Further, the proximal end of the vibrating body unit 10 (the proximal end of the rod-shaped member 45) serves as the antinode position A3 of the ultrasonic vibration. The antinode position A1 is the most distal antinode position placed most distally among the antinode positions (e.g., A1 to A3) of the ultrasonic vibration. Additionally, the antinode position A3 is the most proximal antinode position placed most proximally among the antinode positions (e.g., A1 to A3) of the ultrasonic vibration. In the vibration at the resonance frequency Fr, the node position N1 of the ultrasonic vibration is placed in the cross-sectional area change region 41 of the horn member 37. The node position N1 is placed on the distal direction side with respect to the ultrasonic transducer 31.

In the vibration at the resonance frequency Fr, the proximal end of the horn member 37 serves as the antinode position A2 of the ultrasonic vibration. The antinode position A2 is placed on the proximal direction side with respect to the ultrasonic transducer 31. Furthermore, when, among the antinode positions (e.g., A2 and A3) of the ultrasonic vibration placed on the proximal direction side with respect to the ultrasonic transducer 31, the antinode position which is closest to the ultrasonic transducer 31 is determined as a reference antinode position, the antinode position A2 is the reference antinode position. In this embodiment, the proximal end of the rod-shaped member 45 which is the proximal side transmitting section is placed at a position apart from the antinode position (the reference antinode position) A2 toward the proximal direction by an extending dimension L1 equal to a half wavelength (one time of the half wavelength) of the ultrasonic vibration at the resonance frequency Fr. Thus, the antinode position (the most proximal antinode position) A3 is apart from the antinode position (the reference antinode position) A2 by the extending dimension L1 equal to the half wavelength of the ultrasonic vibration in the axis parallel direction parallel to the longitudinal axis C.

A cross-sectional area reducing section 51 is provided to the rod-shaped member 45, which is the proximal side vibration transmitting section, between the proximal end of the rod-shaped member 45 and the antinode position (the reference antinode position) A2 in the axis parallel direction parallel to the longitudinal axis C. In the rod-shaped member 45, a first transmitting region 52 is extended from the cross-sectional area reducing portion 51 toward the distal direction, and a second transmitting region 53 is extended from the cross-sectional area reducing section 51 toward the proximal direction. Thus, the cross-sectional area reducing section 51 is placed between the first transmitting region 52 and the second transmitting region 53 in the axis parallel direction. In the second transmitting region 53, a cross-sectional area of the rod-shaped member 45 perpendicular to the longitudinal axis C is reduced due to the cross-sectional area reducing section 51 as compared with the first transmitting region 52. In this embodiment, the cross-sectional area reducing section 51 is placed at the node position N2 of the ultrasonic vibration at the resonance frequency Fr.

At a position different from the antinode positions (e.g., A1 to A3) of the ultrasonic vibration, stress caused by the ultrasonic vibration acts. In the vibrating body unit 10, since the cross-sectional area perpendicular to the longitudinal axis C, is reduced at the position where the stress caused by the ultrasonic vibration acts, an amplitude of the ultrasonic vibration increases. Thus, the cross-sectional area of the rod-shaped member 45 (the vibrating body unit 10) perpendicular to the longitudinal axis C is reduced due to the cross-sectional area reducing section 51, and hence the amplitude of the ultrasonic vibration transmitted from the distal direction toward the proximal direction increases. That is, the cross-sectional area reducing section 51 serves as an amplitude increasing section configured to increase the amplitude of the ultrasonic vibration transmitted toward the proximal direction in the rod-shaped member 45.

At the node positions (e.g., N1 and N2) of the ultrasonic vibration, the stress caused by the ultrasonic vibration increases as compared with that at positions other than the node positions. Since the cross-sectional area of the rod-shaped member 45 perpendicular to the longitudinal axis C is reduced at the node position N2 where the stress caused by the ultrasonic vibration is large, a transformation ratio (an increase ratio) of the amplitude of the ultrasonic vibration in the cross-sectional area reducing section 51 rises. Since the transformation ratio of the amplitude of the ultrasonic vibration in the cross-sectional area reducing section 51 rises, a ratio of the amplitude in the second transmitting region 53 relative to the amplitude in the first transmitting region 52 increases. Here, among the node positions (e.g., N2) of the ultrasonic vibration placed on the proximal direction side with respect to the antinode position (the reference antinode position) A2, the node position N2 is closest to the antinode position (the reference antinode position) A2.

Functions and Effects of the ultrasonic treatment apparatus 1 will now be described. At the time of giving a treatment to the treated target, e.g., a biological tissue by using the ultrasonic treatment apparatus 1, the sheath 6, the ultrasonic probe 7, and the jaw 8 are inserted into a body cavity. Further, the treated target is placed between the jaw 8 and the treatment section 17. In this state, the movable handle 13 is closed relative to the fixed handle 12, the jaw 8 closes relative to the treatment section 17, and the treatment target is grasped between the jaw 8 and the treatment section 17. When a supply operation is input by the supply operation input button 16 in a state where the treated target is griped, an electric current is supplied to the ultrasonic transducer 31 from the current supply section 21. Furthermore, the ultrasonic vibration is generated by the ultrasonic transducer 31, and the ultrasonic vibration is transmitted from the proximal direction toward the distal direction in the ultrasonic probe 7. Moreover, the treatment section 17 uses the transmitted ultrasonic vibration to give a treatment, and the treated target is coagulated and incised at the same time as described above. At this time, the generated ultrasonic vibration is transmitted from the distal direction toward the proximal direction in the rod-shaped member 45.

When the treatment is finished, the ultrasonic probe (the distal side vibration transmitting section) 7 having the treatment section 17 provided therein is discarded, and the vibration generating unit 30 (the transducer unit 3) including the expensive piezoelectric elements 32A to 32D is reused. Thus, the ultrasonic probe 7 is replaced in accordance with each treatment. Here, there is a case where a type of a material forming the ultrasonic probe 7 differs depending on each ultrasonic probe. Moreover, there is also a case where even if all the ultrasonic probes 7 are made of Ti-6Al-4V, the content of aluminum differs depending on each ultrasonic probe 7. Thus, the Young's modulus Ea varies in accordance with each ultrasonic probe 7. The young's modulus Ea of the ultrasonic probe 7 affects the resonance frequency Fr of the vibrating body unit 10. Therefore, since the Young's modulus Ea varies in accordance with each ultrasonic probe 7, the resonance frequency Fr of the vibrating body unit 10 changes in accordance with a change in the ultrasonic probe 7 connected to the vibration generating unit 30. That is, the variation in the Young's modulus Ea according to each ultrasonic probe 7 causes a variation in the resonance frequency Fr of the vibrating body unit 10.

Figure 5:
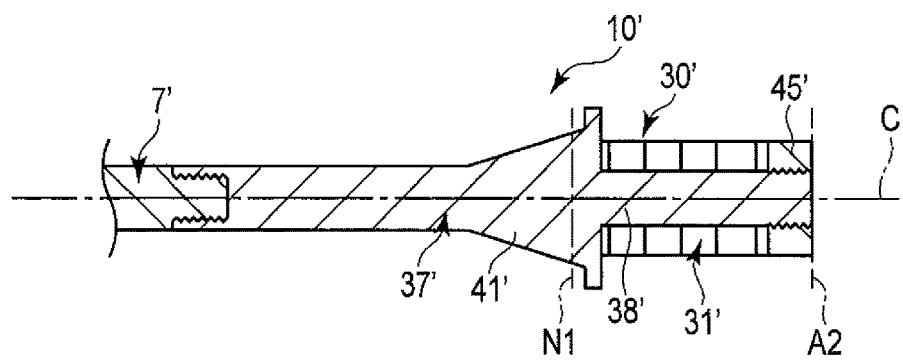
FIG. 5 is a cross-sectional view schematically showing a vibrating body unit according to a comparative example.

Here, as a comparative example, FIG. 5 shows a vibrating body unit 10'. In the vibrating body unit 10', like the vibrating body unit 10 according to the first embodiment, an ultrasonic probe 7', a horn member 37', and an ultrasonic transducer 31' are provided. Furthermore, the vibrating body unit 10' vibrates at a resonance frequency Fr having antinode positions (e.g., A1 and A2) and node positions (e.g., N1). Additionally, the antinode position A1 placed at a distal end of the ultrasonic probe 7' serves as the most distal antinode position. However, in the vibrating body unit 10' (a vibration generating unit 30'), as different from the vibrating body unit 10 (the vibration generating unit 30) according to the first embodiment, the rod-shaped member (the proximal side vibration transmitting section) 45 is not provided, and a back mass 45' is provided instead. The ultrasonic transducer 31' is attached to a transducer attachment section 38' in a state where it is sandwiched between a cross-sectional area change section 41' of the horn member 37' and the back mass 45'.

A position of a proximal end of the back mass 45' coincides with a position of a proximal end of the horn member 37' in the axis parallel direction parallel to the longitudinal axis C. Thus, the proximal end of the horn member 37' serves as the proximal end of the vibrating body unit 10' (the proximal end of the vibration generating unit 30'). Further, in the vibrating body unit 10', the antinode position A2 placed at the proximal end of the vibrating body unit 10' serves as the most proximal antinode position, and one antinode position A2 alone is placed on the proximal direction side with respect to the ultrasonic transducer 31'. Thus, a dimension in the axis parallel direction of the vibrating body unit 10' (the vibration generating unit 30') is smaller than that of the vibrating body unit 10 (the vibration generating unit 30) according to the first embodiment by a half wavelength of the ultrasonic vibration.

In the vibrating body unit 10', since the dimension in the axis parallel direction of the vibration generating unit 30' is small, an influence of the Young's modulus Eb of the vibration generating unit 30' an the resonance frequency Fr of the vibrating body unit 10' is small. Thus, a variation in the Young's modulus Ea of each ultrasonic probe 7' greatly affects the resonance frequency Fr of the vibrating body unit 10'.

Thus, in this embodiment, to reduce the influence of the variation in the Young's modulus Ea according to each ultrasonic probe 7 on the resonance frequency Fr of the vibrating body unit 10, the rod-shaped member (the proximal side vibration transmitting section) 45 is provided. When the rod-shaped member 45 is provided, the Young's modulus Ec of the rod-shaped member 45 affects the resonance frequency Fr of the vibrating body unit 10. That is, since the dimension in the axis parallel direction becomes larger than that in the case where the rod-shaped member 45 is not provided (the comparative example in FIG. 5) by the half wavelength of the ultrasonic vibration, the influence of the Young's modulus Eb of the vibration generating unit 30 on the resonance frequency Fr of the vibrating body unit 10 increases. Thus, as compared with the comparative example in FIG. 5, the influence of the variation in the Young's modulus Ea according to each ultrasonic probe 7 on the resonance frequency Fr of the vibrating body unit 10 becomes smaller.

Furthermore, in the rod-shaped member 45 which is the proximal side vibration transmitting section, an amplitude of the ultrasonic vibration transmitted from the distal direction toward the proximal direction is increased by the cross-sectional area reducing section 51. Thus, in the second transmitting region 53 extended in apart located on the proximal direction side of the cross-sectional area reducing section 51, the amplitude of the ultrasonic vibration becomes large. As a result of the above verification of the vibration state, the influence of the Young's modulus (E) on the resonance frequency (Fr) becomes considerable in a region where the amplitude of the ultrasonic vibration increases. Since the second transmitting region 53 where the amplitude of the ultrasonic vibration is large is provided in the rod-shaped member 45, the influence of the Young's modulus Ec of the rod-shaped member 45 on the resonance frequency Fr of the vibrating body unit 10 increases, and the influence of the Young's modulus Eb of the vibration generating unit 30 on the resonance frequency Fr of the vibrating body unit 10 further becomes significant. Thus, the influence of the variation in the Young's modulus Ea according to each ultrasonic probe 7 on the resonance frequency Fr of the vibrating body unit 10 is further lowered. Consequently, even if the variation in the Young's modulus Ea occurs in accordance with each ultrasonic probe 7 which is the distal side vibration transmitting section, the variation in the resonance frequency Fr of the vibrating body unit 10 can be reduced.

Further, at the node positions (e.g., N1 and N2) of the ultrasonic vibration including the node position N2 placed at the cross-sectional area reducing section 51, stress caused by the ultrasonic vibration is larger than that at any other position than the node positions. Since the cross-sectional area reducing section 51 is provided at the node position N2 where the stress of the ultrasonic vibration is large, the transformation ratio (the increase ratio) of the amplification of the ultrasonic vibration in the cross-sectional area reducing section 51 becomes high. When the transformation ratio of the amplitude of the ultrasonic vibration in the cross-sectional area reducing section 51 becomes high, the amplitude in the second transmitting region 53 increases. Consequently, the influence of the Young's modulus Ec of the rod-shaped member 45 on the resonance frequency Fr of the vibrating body unit 10 further increases, the influence of the variation in the Young's modulus Ea according to each ultrasonic probe 7 on the resonance frequency Fr of the vibrating body unit 10 is reduced. As a result, even if the variation in the Young's modulus Ea occurs in accordance with each ultrasonic probe 7 which is the distal side vibration transmitting section, the variation in the resonance frequency Fr of the vibrating body unit 10 can be further effectively decreased.

Modification of First Embodiment

Figure 6:
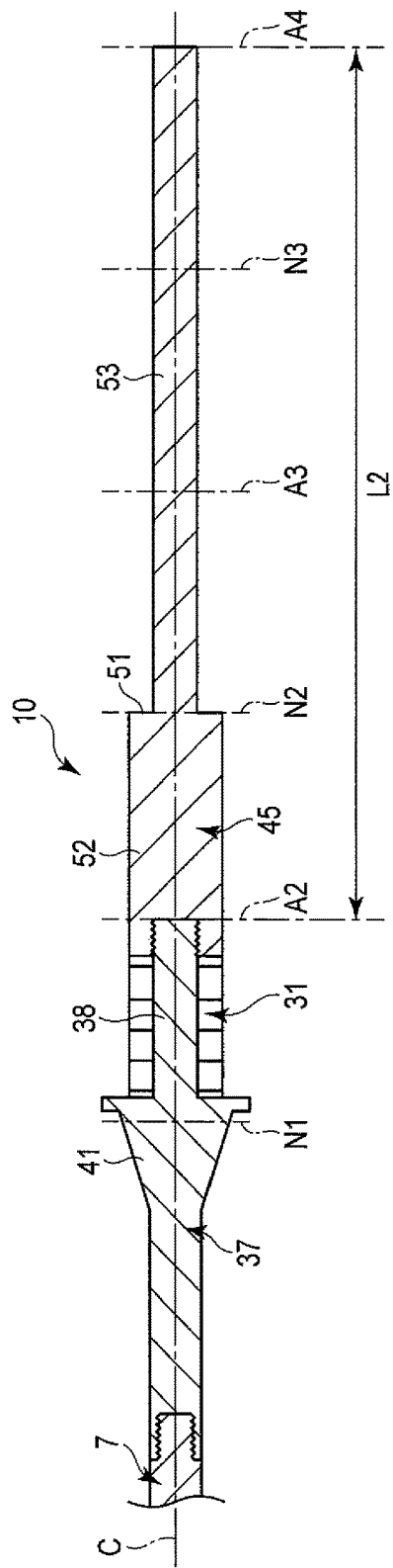
FIG. 6 is a cross-sectional view schematically showing a vibrating body unit according to a first modification of the first embodiment.

It is to be noted that, in the first embodiment, the proximal end of the rod-shaped member 45 (the proximal end of the vibrating body unit 10) is placed at the position apart from the antinode position (the reference antinode position) A2 toward the proximal direction by the half wavelength of the ultrasonic vibration, but it is not restricted thereto. For example, as a first modification of the first embodiment, the proximal end of the rod-shaped member 45 (the proximal end of the vibrating body unit 10) may be placed at a position apart from the antinode position (the reference antinode position) A2 toward the proximal direction by an extending dimension L2 equal to one wavelength (two times of the half wavelength) of the ultrasonic vibration at the resonance frequency Fr as shown in FIG. 6. The vibrating body unit 10 according to this modification vibrates at the resonance frequency Fr having the antinode positions (e.g., A1 to A4) and the node positions (e.g., N1 to N3).

The antinode position A1 placed at the distal end of the ultrasonic probe 7 serves as the most distal antinode position, and the antinode position A4 placed at the proximal end of the rod-shaped member 45 serves as the most proximal antinode position. Furthermore, the antinode position (the reference antinode position) A2 is placed at the proximal end of the horn member 37, and it is an antinode position that is closest to the ultrasonic transducer 31 among the antinode positions (e.g., A2 to A4) of the ultrasonic vibration placed on the proximal direction side with respect to the ultrasonic transducer 31. Thus, in this modification, a dimension of the rod-shaped member 45 (the vibrating body unit 10) in the axis parallel direction parallel to the longitudinal axis C is longer than that in the first embodiment by the half wavelength.

Moreover, in this modification, likewise, the cross-sectional area reducing section 51 which is an amplitude increasing section is provided at the node position N2 between the antinode position A2 and the antinode position A3. In this modification, the second transmitting region 53 is extended toward the proximal direction until it reaches the antinode position (the most proximal antinode position) A4 through the antinode position A3. In this modification, the node position N2 is closest to the antinode position (the reference antinode position) A2 among the node positions (e.g., N2 and N3) of the ultrasonic vibration placed on the proximal direction side with respect to the antinode position (the reference antinode position) A2. With the above-described configuration, a dimension of the second transmitting region 53 in the axis parallel direction is longer than that in the first embodiment by the half wavelength.

When the dimension of the second transmitting region 53 in the axis parallel direction increases, a volume of the second transmitting region 53 where the ultrasonic vibration has a large amplitude increases. According to the above verification of the vibration state, the influence of the Young's modulus (F) on the resonance frequency (Fr) increases in a region having a larger volume. Since the volume of the second transmitting region 53 increases in the rod-shaped member 45, as compared with the first embodiment, the influence of the Young's modulus Ec of the rod-shaped member 45 on the resonance frequency Fr of the vibrating body unit 10 becomes large, and the influence of the Young's modulus Eb of the vibration generating unit 30 on the resonance frequency Fr of the vibrating body unit 10 further increases. Thus, the influence of the variation in the Young's modulus Ea according to each ultrasonic probe 7 on the resonance frequency Fr of the vibrating body unit 10 is further reduced. Consequently, even if a variation in the Young's modulus Ea occurs in accordance with each ultrasonic probe 7 which is the distal side vibration transmitting section, a variation in the resonance frequency Fr of the vibrating body unit 10 can be further effectively lowered.

Second Embodiment

A second embodiment according to the present invention will now be described with reference to FIG. 7. The second embodiment is provided by modifying the configuration of the first embodiment as follows. It is to be noted that like reference numerals denote parts equal to those in the first embodiment to omit a description thereof.

Figure 7:
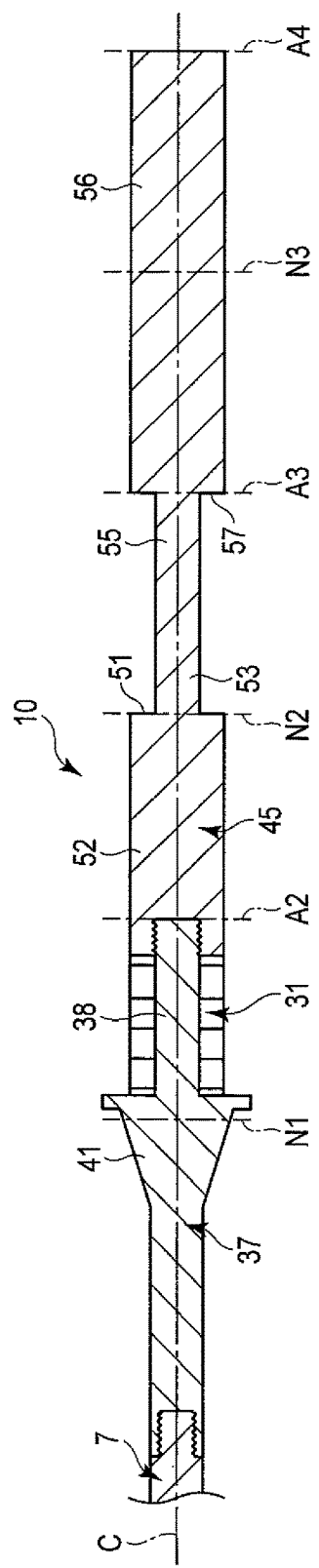
FIG. 7 is a cross-sectional view schematically showing a vibrating body unit according to a second embodiment.

FIG. 7 is a view showing a configuration of a vibrating body unit 10 according to the second embodiment. As shown in FIG. 7, the vibrating body unit 10 according to this embodiment vibrates at a resonance frequency Fr having antinode positions (e.g., A1 to A4) and node positions (e.g., N1 to N3). The antinode position A1 placed at a distal end of an ultrasonic probe 7 serves as the most distal antinode position, and the antinode position A4 placed at a proximal end of a rod-shaped member 45 serves as the most proximal antinode position. Further, the antinode position (a reference antinode position) A2 is placed at a proximal end of a horn member 37, and it is an antinode position that is closest to an ultrasonic transducer 31 among the antinode positions (e.g., A2 to A4) of an ultrasonic vibration placed on the proximal direction side with respect to the ultrasonic transducer 31. Thus, in this embodiment, a dimension of the rod-shaped member 45 (the transducer unit 10) in an axis parallel direction parallel to a longitudinal axis C is longer than that in the first embodiment by a half wavelength.

Furthermore, in this embodiment, likewise, a cross-sectional area reducing section 51 which is an amplitude increasing section is provided at the node position N2 between the antinode position A2 and the antinode position A3. The node position N2 is closest to the antinode position (the reference antinode position) A2 among the node positions (e.g., N2 and N3) of the ultrasonic vibration placed on the proximal direction side with respect to the antinode position (the reference antinode position) A2.

Furthermore, in this embodiment, a first extending region 55 is continuous on the proximal direction side of a second transmitting region 53. Thus, the first extending region 55 is placed on the proximal direction side with respect to the cross-sectional area reducing section 51 which is the amplitude increasing section. The second transmitting region 53 and the first extending region 55 are extended between the node position N2 and the antinode position A3. Moreover, a second extending region 56 is provided on the proximal direction side of the first extending region 55 in the rod-shaped member 45. The second extending region 56 is extended from the antinode position A3 toward the proximal direction. Additionally, the second extending region 56 is extended to the antinode position (the most proximal antinode position) A4 placed at the proximal end of the rod-shaped member 45 (the proximal end of the vibrating body unit 10).

A cross-sectional area increasing section 57 is provided between the first extending region 55 and the second extending region 56 in the axis parallel direction that is parallel to the longitudinal axis C. A cross-sectional area of the rod-shaped member 45 perpendicular to the longitudinal axis C in the second extending region 56 is enlarged by the cross-sectional area increasing section 57 compared that in the first extending region 55. Consequently, a volume of the second extending region 56 increases. In the vibration at a resonance frequency Fr, the antinode position (a cross section change antinode position) A3 is placed at the cross-sectional area increasing section 57. The antinode position (the cross section change antinode position) A3 is one of the antinode positions of the ultrasonic vibration placed between the cross-sectional area reducing section 51 as the amplitude increasing section and the proximal end of the rod-shaped member 45 in the axis parallel direction. Further, the antinode position (the cross section change antinode position) A3 is closest to the cross-sectional area reducing section (the amplitude increasing section) 51 among the antinode positions (e.g., A3 and A4) of the ultrasonic vibration placed on the proximal direction side with respect to the cross-sectional area reducing section 51.

At the antinode positions (e.g., A1 to A4) of the ultrasonic vibration including the antinode position A3 at which the cross-sectional area increasing section 57 is placed, stress caused by the ultrasonic vibration becomes zero. Since the stress caused by the ultrasonic vibration does not act, at the cross-sectional area increasing section 57, the amplitude of the ultrasonic vibration is not reduced (not changed) even if the cross-sectional area perpendicular to the longitudinal axis C increases (varies). Thus, the ultrasonic vibration is transmitted from the first extending region 55 to the second extending region 56 without reducing its amplitude. That is, in a state where the amplitude increased by the cross-sectional area reducing section 51 is maintained, the ultrasonic vibration is transmitted to the second extending region 56. Thus, in the second extending region 56, the amplitude of the ultrasonic vibration increases.

In this embodiment, the second extending region 56 where the amplitude is large and the cross-sectional area perpendicular to the longitudinal axis C (i.e., a volume) is large is extended in the rod-shaped member 45 over the half wavelength of the ultrasonic vibration. According to a result of the above verification of the vibration state, an influence of the Young's modulus (E) on the resonance frequency (Fr) becomes more prominent in a region having a larger amplitude of the ultrasonic vibration, and an influence of the Young's modulus (E) on the resonance frequency (Fr) becomes more prominent in a region having a larger volume. Since the second extending region 56 where the amplitude is large and the volume is also large is provided in the rod-shaped member 45, as compared with the first embodiment, the influence of the Young's modulus Ec of the rod-shaped member 45 on the resonance frequency Fr of the vibrating body unit 10 becomes prominent, and the influence of the Young's modulus Eb of the vibration generating unit 30 on the resonance frequency Fr of the vibrating body unit 10 becomes further considerable. Thus, an influence of a variation in the Young's modulus Ea according to each ultrasonic probe 7 on the resonance frequency Fr of the vibrating body unit 10 is further reduced. Consequently, even if the variation in the Young's modulus Ea occurs in accordance with each ultrasonic probe 7 which is a distal side vibration transmitting section, the variation in the resonance frequency Fr of the vibrating body unit 10 can be further effectively reduced.

Furthermore, among the antinode positions (e.g., A3 and A4) of the ultrasonic vibration placed on the proximal direction side with respect to the cross-sectional area reducing section 51, the antinode position (the cross section change antinode position) A3 placed at the cross-sectional area increasing section 55 is closest to the cross-sectional area reducing section (the amplitude increasing section) 51. With the above-described configuration, a dimension of the second extending region 56 in the axis parallel direction becomes large, and the volume of the second extending region 56 can be further increased.

Comparison of Comparative Example, First Embodiment, and Second Embodiment

FIG. 8 is a view showing a relationship between the Young's modulus Ea of the ultrasonic probe 7 (7') and the resonance frequency Fr of the vibrating body unit 10 (10') in each of a comparative example, the first embodiment, and the second embodiment. As shown in FIG. 8, a variation occurs in the Young's modulus Ea of the ultrasonic probe 7 (7') connected to the vibration generating unit 30 (30') between a maximum value Eamax and a minimum value Eamin. In the comparative example, the resonance frequency Fr of the vibrating body unit 10' varies between a maximum value Fr1max and a minimum value Fr1min. On the other hand, in the first embodiment, the resonance frequency Fr of the vibrating body unit 10 varies between a maximum value Fr2max and a minimum value Fr2min, the variation in the resonance frequency Fr of the vibrating body unit 10 (10') is smaller than that in the comparative example. Moreover, in the second embodiment, the resonance frequency Fr of the vibrating body unit 10 varies between a maximum value Fr3max and a minimum value Fr1min, and the variation in the resonance frequency Fr of the vibrating body unit 10 becomes further smaller than that in the first embodiment.

It is to be noted that, in FIG. 8, an axis of abscissa represents the Young's modulus Ea of the ultrasonic probe 7 (7'), and an axis of ordinate represents the resonance frequency Fr of the vibrating body unit 10 (10'). Thus, in the first embodiment, an inclination of a straight line is smaller than that in the comparative example. Additionally, in the second embodiment, an inclination of a straight line is smaller than that in the first embodiment.

Third Embodiment

A third embodiment according to the present invention will now be described with reference to FIG. 9 and FIG. 10. The third embodiment is provided by modifying the configuration of the first embodiment as follows. It is to be noted that like reference numerals denote parts equal to those in the first embodiment to omit a description thereof.

Figure 9:
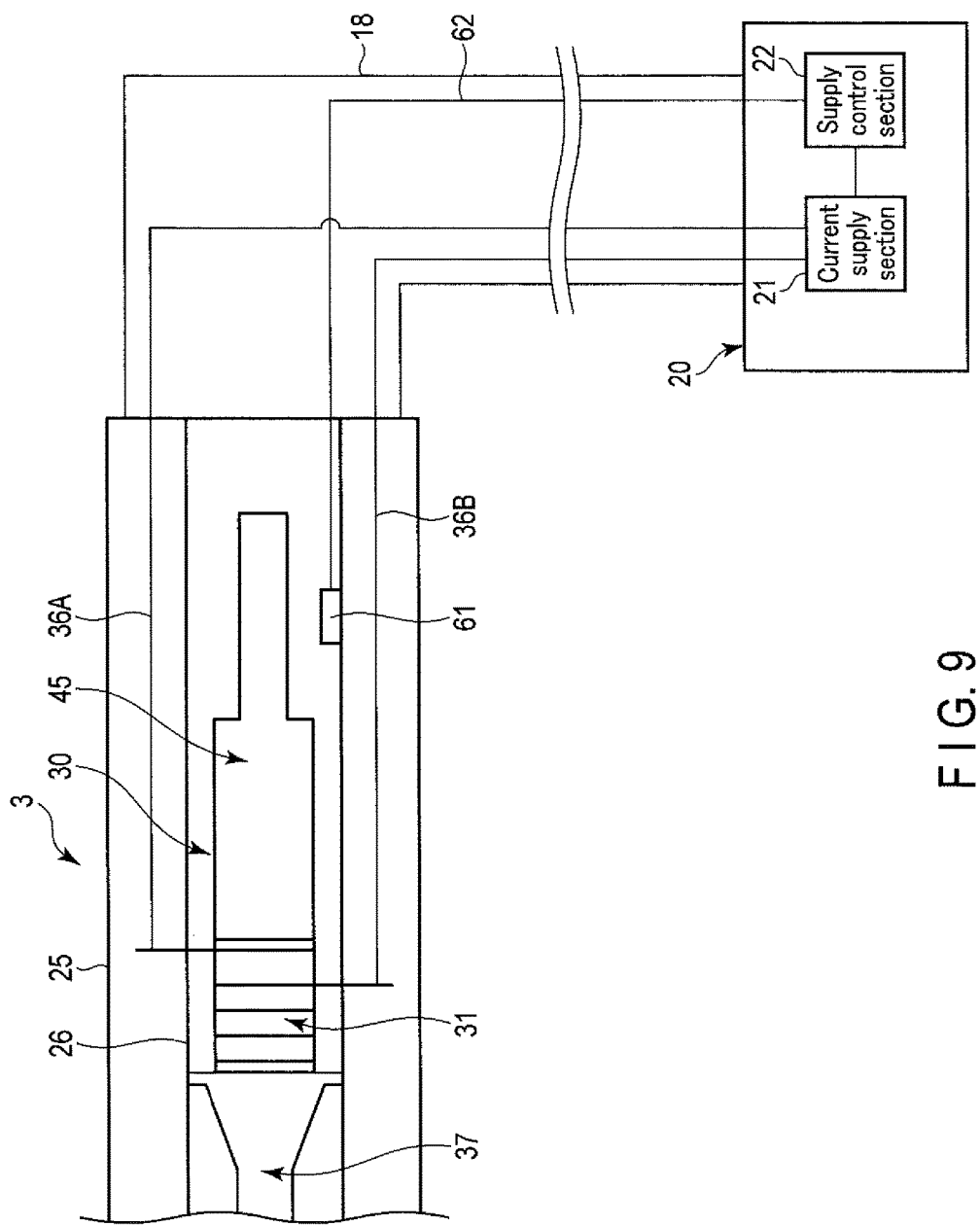
FIG. 9 is a schematic view showing a configuration of a transducer unit and an electric power supply unit according to a third embodiment.

FIG. 9 is a view showing a configuration of a transducer unit 3 and an electric power supply unit 20 according to this embodiment. As shown in FIG. 9, in this embodiment, a memory 61 which is a storage section is provided in a vibration generating unit 30. Vibration characteristics provided by ultrasonic vibration of the vibration generating unit 30 are stored in the memory 61. For example, information concerning the Young's modulus Eb of the vibration generating unit 30, a standard value of a resonance frequency Fr of a vibrating body unit 10, and others are stored in the memory 61.

In the vibration generating unit 30 formed of a horn member 37, an ultrasonic transducer 31, and a rod-shaped member 45, the Young's modulus Eb varies in accordance with each vibration generating unit 30 for the same reason as that of the ultrasonic probe 7. Even if an influence of a variation in the Young's modulus Ea of each ultrasonic probe 7 on the resonance frequency Fr of the vibrating body unit 10 is small, a vibration frequency Fr varies due to the variation in the Young's modulus Eb of each vibration generating unit 30. Thus, measurement of the resonance frequency Fr of the vibrating body unit 10 performed by a supply control section 22 of the electric power supply unit 20 becomes complicated.

Figure 10:
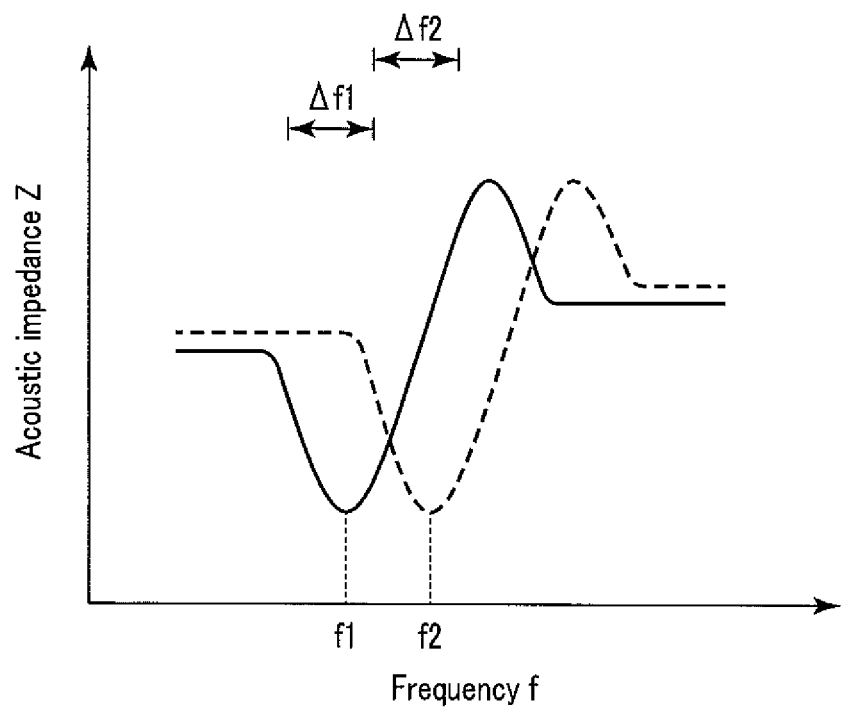
FIG. 10 is a schematic view showing an example of a relationship between a frequency of an ultrasonic vibration and an acoustic impedance.

FIG. 10 is a view showing a relationship between a frequency f of the ultrasonic vibration and an acoustic impedance Z. The acoustic impedance Z changes in accordance with a vibration state of the vibrating body unit 10. Thus, as shown in FIG. 10, the acoustic impedance Z changes by a change in the frequency f of the ultrasonic vibration. Further, the relationship between the frequency f of the ultrasonic vibration and the acoustic impedance Z changes in accordance with a change in the Young's modulus Eb of the vibration generating unit 30. For example, when one vibration generating unit 30 (the vibration generating unit 30 having the Young's modulus Eb1) is used in the vibrating body unit 10, the relationship between the frequency f of the ultrasonic vibration and the acoustic impedance Z changes as indicated by a solid line in FIG. 10. Furthermore, when another vibration generating unit 30 (the vibration generating unit 30 having the Young's modulus Eb2) is used in the vibrating body unit 10, the relationship between the frequency f of the ultrasonic vibration and the acoustic impedance Z changes as indicated by a dotted line in FIG. 10.

In a treatment, the supply control section 22 controls an electric current supplied from a current supply section 21 to an ultrasonic transducer 31, and measures the resonance frequency Fr of the vibrating body unit 10 by performing a PLL (Phase Lock Loop) control. That is, a frequency f at which the acoustic impedance Z becomes minimum in a predetermined frequency domain (e.g., Δf1 or Δf2) of the ultrasonic vibration is detected as the resonance frequency Fr. For example, when the vibration generating unit 30 having the Young's modulus Eb1 is used in the vibrating body unit 10, a frequency f1 is detected as the resonance frequency Fr. Furthermore, when the vibration generating unit 30 having the Young's modulus Eb2 is used in the vibrating body unit 10, a frequency f2 is detected as the resonance frequency Fr.

The memory 61 is connected to the supply control section 22 through an electrical signal line 62. The supply control section 22 controls a supply state of the electric current from the current supply section 21 based on vibration characteristics of the vibration generating unit 30 stored in the memory 61. Moreover, the supply control section 22 measures the resonance frequency Fr of the vibrating body unit 10, in which the ultrasonic probe 7 is connected to the vibration generating unit 30, based on the vibration characteristics of the vibration generating unit 30. Since the resonance frequency Fr of the vibrating body unit 10 is measured based on the vibration characteristics of the vibration generating unit 30, the supply control section 22 measures the resonance frequency Fr in a predetermined frequency domain (e.g., Δf1 or Δf2) near the resonance frequency Fr, but does not perform the measurement in frequency domains greatly deviating from the resonance frequency Fr. Thus, the measurement of the resonance frequency Fr of the vibrating body unit 10 is appropriately and readily performed by the supply control section 22 of the electric power supply unit 20, and the electric current is appropriately supplied from the current supply section 21 in the electric power supply unit 20 to the ultrasonic transducer 31. Thus, treatment performance in a treatment using the ultrasonic vibration can be effectively assured.

Other Modifications

Figure 11:
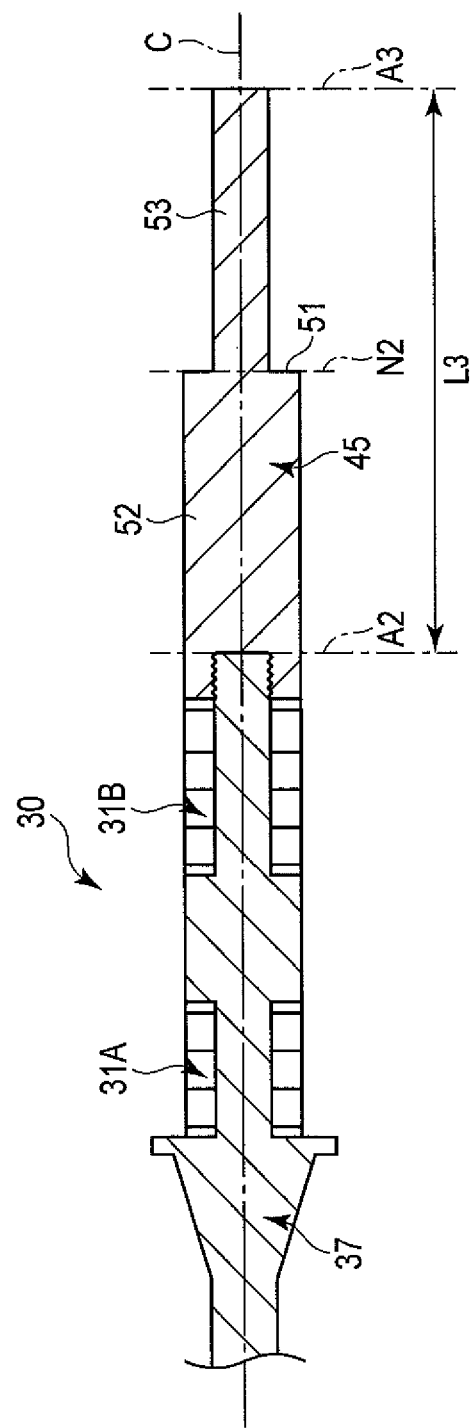
FIG. 11 is a cross-sectional view schematically showing a vibration generating unit according to a one modification of the first embodiment to the third embodiment.

It is to be noted that only one ultrasonic transducer 31 is provided in the vibration generating unit 30 in the foregoing embodiments and modification, but it is not restricted thereto. For example, as one modification of the foregoing embodiments, multiple (two in this modification) ultrasonic transducers 31A and 31B may be provided in the vibration generating unit 30 as shown in FIG. 11. The ultrasonic transducers 31A and 31B are placed apart from each other in the axis parallel direction parallel to the longitudinal axis C. In this modification, an antinode position A3 is the most proximal antinode position. Further, the ultrasonic transducer 31B serves as the most proximal transducer placed most proximally among the ultrasonic transducer (e.g., 31A and 31B). An antinode position A2 is placed on the proximal direction side with respect to the ultrasonic transducer (the most proximal vibrator) 31B. Furthermore, the antinode position (a reference antinode position) A2 is an antinode position which is closest to the ultrasonic vibrator 31B among antinode positions (e.g., A2 and A3) of the ultrasonic vibration placed on the proximal direction side with respect to the ultrasonic transducer (the most proximal transducer) 31B.

Moreover, a proximal end of a rod-shaped member 45 (a proximal end of a vibrating body unit 10) is placed to be apart from the antinode position (the reference antinode position) A2 in the proximal direction by an extending dimension L3 equal to a half wavelength of the ultrasonic vibration at a resonance frequency Fr. Additionally, a cross-sectional area reducing section 51 which is an amplitude increasing section is provided between the proximal end of the rod-shaped member 45 (the antinode position A3) and the antinode position (the reference antinode position) A2 in the axis parallel direction. In this modification, like the first embodiment, a node position N2 of the ultrasonic vibration at the resonance frequency Fr is placed at the cross-sectional area reducing section 51.

Figure 12:
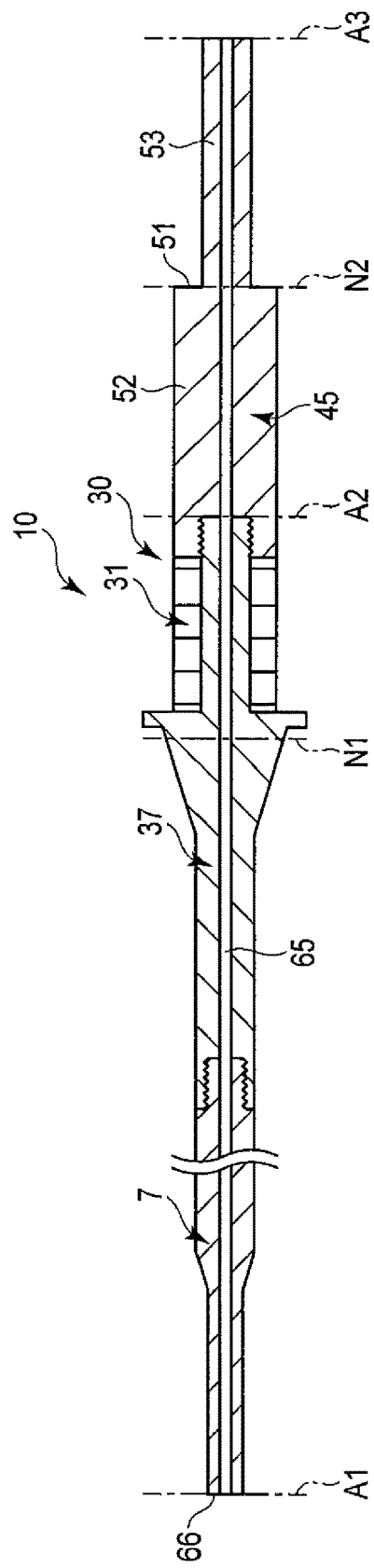
FIG. 12 is a cross-sectional view schematically showing a vibrating body unit according to another modification of the first embodiment to the third embodiment.

Further, the treatment section 17 of the vibrating body unit 10 is used for ultrasonic incising-and-coagulation in the foregoing embodiment and modification, but it is not restricted thereto. For example, as another modification of the foregoing embodiments, a path section 65 may be formed in the vibrating body unit 10 along the longitudinal axis C as shown in FIG. 12. Since the path section 65 is formed, the vibrating body unit 10 is formed into a hollow tubular shape. In this modification, a distal face 66 of the vibrating body unit 10 is used as a treatment section. When the vibrating body unit 10 vibrates in a state where a liquid such as a physiological saline is being supplied to a distal portion of an ultrasonic probe 7, cavitation occurs near the distal face 66. The cavitation that has occurred is used to shatter and emulsify a treated target such as a biological tissue. Furthermore, the shattered and emulsified treated target is sucked and collected through the path section 65. As described above, in this modification, the vibrating body unit 10 is used in an ultrasonic suction treatment. In this modification, like the foregoing embodiments and modification, an influence of a variation in the Young's modulus Ea according to each ultrasonic probe 7 on the resonance frequency Fr of the vibrating body unit 10 is lowered.

Moreover, although the description has been given as to the influence of the Young's modulus Ea of the ultrasonic probe 7 on the resonance frequency Fr of the vibrating body unit 10 in the foregoing embodiments and modification, physical properties other than the Young's modulus Ea such as a Poisson ratio, density, or the like of the ultrasonic probe 7 also affect the resonance frequency Fr of the vibrating body unit 10. In the foregoing embodiments and modification, providing the rod-shaped member (the proximal side vibration transmitting section) 45 and the cross-sectional area reducing section (the amplitude increasing section) 51 in the vibration generating unit 30 reduces the influence of the Young's modulus Ea of the ultrasonic probe 7 as well as the Poisson ratio or density on the resonance frequency Fr of the vibrating body unit 10.

Based on the foregoing embodiments and modification, the proximal end of the proximal side vibration transmitting section (45) could be placed at a position part from the reference antinode position (A2) by the extending dimension (L1; L2) equal to an integral multiple of the half wavelength of the ultrasonic vibration. Here, among the antinode positions (A2, A3; A2 to A4) placed on the proximal direction side with respect to the ultrasonic transducer (31), the reference antinode position (A2) is an antinode position closest to the ultrasonic transducer (31; 31B). Moreover, the amplitude increasing section (51) that increases the amplitude of the ultrasonic vibration transmitted toward the proximal direction could be provided between the proximal end of the proximal side vibration transmitting section (45) and the reference antinode position (A2) in the axis parallel direction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibration generating unit with which a distal side vibration transmitting section is connected from a distal direction side, the distal side vibration transmitting section including a treatment section configured to treat a biological tissue and provided in a distal portion thereof, and the vibration generating unit being configured to generate an ultrasonic vibration transmitted to the distal side vibration transmitting section so that the vibration generating unit vibrates at a resonance frequency in a predetermined frequency domain, the vibration generating unit comprising:
a connecting section with which the distal side vibration transmitting section is connected;
an ultrasonic transducer including a piezoelectric element which is configured to generate the ultrasonic vibration;
a transducer attachment section to which the ultrasonic transducer is attached;
a proximal side vibration transmitting section which is extended from a proximal end of the ultrasonic transducer toward a proximal direction along a longitudinal axis, the proximal side vibration transmitting section being separable from the transducer attachment section while the ultrasonic transducer is attached to the transducer attachment section, and a proximal end of the proximal side vibration transmitting section being placed at a position apart from a reference antinode position toward the proximal direction by an extending dimension equal to an integral multiple of a half wavelength of the ultrasonic vibration at the resonance frequency in the predetermined frequency domain, when the reference antinode position is an antinode position closest to the ultrasonic transducer among antinode positions of the ultrasonic vibration at the resonance frequency in the predetermined frequency domain placed on a proximal direction side with respect to the ultrasonic transducer; and
an amplitude increasing section which is provided between the proximal end of the proximal side vibration transmitting section and the reference antinode position in an axis parallel direction that is parallel to the longitudinal axis, and which is configured to increase an amplitude of the ultrasonic vibration transmitted toward the proximal direction in the proximal side vibration transmitting section, the amplitude increasing section being placed at a node position closest to the reference antinode position among node positions of the ultrasonic vibration at the resonance frequency in the predetermined frequency domain placed on the proximal direction side with respect to the reference antinode position, wherein:
the proximal side vibration transmitting section includes:
a first extending region provided on the proximal direction side with respect to the amplitude increasing section;
a second extending region provided on the proximal direction side with respect to the first extending region; and
a cross-sectional area increasing section which is provided between the first extending region and the second extending region in the axis parallel direction, and which is configured to increase a cross-sectional area of the proximal side vibration transmitting section perpendicular to the longitudinal axis in the second extending region to be larger than that in the first extending region, the cross-sectional area increasing section being placed at a cross section change antinode position which is one of the antinode positions of the ultrasonic vibration placed between the amplitude increasing section and the proximal end of the proximal side vibration transmitting region in the axis parallel direction.

2. The vibration generating unit according to claim 1, wherein
the proximal side vibration transmitting section includes a first transmitting region extended from the amplitude increasing section toward a distal direction, and a second transmitting region extended from the amplitude increasing section toward the proximal direction, and
the amplitude increasing section includes a cross-sectional area reducing section which is provided between the first transmitting region and the second transmitting region in the axis parallel direction, and which is configured to reduce a cross-sectional area of the proximal side vibration transmitting section perpendicular to the longitudinal axis in the second transmitting region to be smaller than that in the first transmitting region.

3. The vibration generating unit according to claim 1, wherein
the cross section change antinode position is closest to the amplitude increasing section among the antinode positions of the ultrasonic vibration placed on the proximal direction side with respect to the amplitude increasing section.

4. The vibration generating unit according to claim 1, wherein
the ultrasonic transducer is ultrasonic transducers placed apart from each other in the axis parallel direction, and
when the ultrasonic transducer placed most proximally among the ultrasonic transducers is determined as a most proximal transducer, the reference antinode position is an antinode position closest to the most proximal transducer among the antinode positions of the ultrasonic vibration placed on the proximal direction side with respect to the most proximal transducer.

5. A vibrating body unit comprising:
the vibration generating unit according to claim 1; and
the distal side vibration transmitting section which is extended in a part located on the distal direction side of the vibration generating unit along the longitudinal axis, and which is configured to transmit the ultrasonic vibration from the proximal direction toward a distal direction, the distal side vibration transmitting section including the treatment section to which the ultrasonic vibration is transmitted in the distal portion thereof.

6. An ultrasonic treatment apparatus comprising:
the vibrating body unit according to claim 5; and
an electric power supply unit including a current supply section which is configured to supply an electric current to the ultrasonic transducer.

7. The ultrasonic treatment apparatus according to claim 6, wherein
the vibration generating unit includes a storage section which is configured to store vibration characteristics provided by the ultrasonic vibration of the vibration generating unit, and
the electric power supply unit includes a supply control section which is configured to control a supply state of the electric current from the current supply section based on the vibration characteristics of the vibration generating unit stored in the storage section, and which is configured to measure a resonance frequency of the vibrating body unit in which the distal side vibration transmitting section is connected to the vibration generating unit, based on the vibration characteristics of the vibration generating unit.

8. The vibration generating unit according to claim 1, wherein the piezoelectric element of the ultrasonic transducer is configured to generate the ultrasonic vibration which performs a longitudinal vibration, and
the proximal side vibration transmitting section is configured to transmit the ultrasonic vibration, which performs the longitudinal vibration, from a distal direction toward the proximal direction.

* * * * *